United States Patent [19]
Fritz et al.

[11] Patent Number: 5,861,377
[45] Date of Patent: Jan. 19, 1999

[54] ANTISTASIN TYPE SERINE PROTEASE INHIBITORS

[75] Inventors: Hans Fritz, Icking; Christian Sommerhoff, München, both of Germany; Jutta Heim, Ramlinsburg, Switzerland

[73] Assignee: Novartis AG, Basel, Switzerland

[21] Appl. No.: 369,829

[22] Filed: Jan. 6, 1995

[30] Foreign Application Priority Data

Jan. 7, 1994 [EP] European Pat. Off. ............. 94810006

[51] Int. Cl.$^6$ .......................... C07K 14/81; A61K 38/55; A61K 38/57
[52] U.S. Cl. .................................. 514/12; 514/2; 514/24; 530/324; 530/345; 435/69.1; 435/69.2
[58] Field of Search .................................. 514/2, 21, 12; 530/324, 345; 930/210, 250; 435/69.2, 69.1

[56] References Cited

U.S. PATENT DOCUMENTS

| | | | |
|---|---|---|---|
| 4,588,587 | 5/1986 | Gasic | 514/21 |
| 4,668,662 | 5/1987 | Tripier | 514/12 |
| 4,835,253 | 5/1989 | Burton | 530/330 |

FOREIGN PATENT DOCUMENTS

| | | |
|---|---|---|
| 0404055 | 12/1990 | European Pat. Off. . |
| 0454372 A | 10/1991 | European Pat. Off. . |
| 94810750 | 4/1995 | European Pat. Off. . |
| 0662514 A1 | 12/1995 | European Pat. Off. . |
| WO90/12808 | 4/1990 | WIPO . |
| WO 94/23709 | 10/1994 | WIPO . |

OTHER PUBLICATIONS

Condra et al. Isolation and structural characterization of a potent inhibitor of coagulation Factor Xa from the leech *Haementeria ghilianii*. Thrombosis and Haemostasis. vol. 61, No. 3, pp. 437–441, 1989.

Nutt et al. Purification and characterization of recombinant antistasin: a leech–derived inhibitor of coagulation Factor Xa. Archives of Biochemistry and Biophysics. vol. 285, No. 1, pp. 37–44, Feb. 15, 1991.

Holt et al. Antistasin, and inhibitor of coagulation and metastasis, binds to sulfatide (Gal(3–SO$_4$)β1–1Cer) and has a sequence homology with other proteins that bind sulfated glycoconjugates. The Journal of Biological Chemistry. vol.264, No. 21, pp. 12138–12140, 1989.

Hofmann et al. Site–directed mutagenesis of the leech–derived Factor Xa inhibitor antistasin. Biochemical Journal. vol.287, pp. 943–949, 1992.

Blankenship et al. Amino acid sequence of ghilanten: anti-coagulant–antimetastatic principle of the South American leech, *haementeria ghilianii*. Biochemical and Biophysical Research Communications. vol. 166, No. 3, pp. 1384–1389, Feb. 14, 1990.

Söllner, C., et al., "Isolation and characterization of hirustasin, an antistasin–type serine–proteinase inhibitor from the medical leech *Hirudo medicinalis*", *Europ. J. Biochem.*, 219:937–943 (1994).

Achstetter T. and Wolf D. H., "Proteinases, Proteolysis and Biological Control in the Yeast *Saccharomyces cerevisiae*", *Yeast*, 1:139–157 (1985).

Ako, H., et al., The Preparation of Anhydro–trypsin and Its Reactivity with Naturally Occurring Proteinase Inhibitors:, *Biochem. Biophys. Res. Com.*, 47(6):1402–1407 (1972).

Baskova, I.P., et al., Abstract 74160, "Inhibition of Human Blood Plasma Kallikrein by Salivary Gland Secretion and Extracts of the Medicinal Leech", *Biological Abstracts*, 87(7):AB795 (1989).

Bieth, J.G., "Pathophysiological Interpretation of Kinetic Constants of Protease Inhibitors", *Europ. Physopat. Resp.*, 16:183–195 (1980).

Chase, T. Jr., et al., "Titration of Trypsin, Plasmin, and Thrombin with p–Nitrophenyl p'–Guanidinobenzoate HCl", *Methods Enzymol.*, XIX:20–27 (1970).

Dunwiddie, C., et al., "Antistasin, a Leech–deriuved Inhibitor of Factor Xa—Kinetic Analysis of Enzyme Inhibition and Identification of the Reactive Site", *J. Biol. Chem.*, 264(28) 16694–16699 (1989).

Friedman, M., et al., "The Chromatographic Determination of Cystine and Cysteine Residues in Proteins as S–β–(4–Pyridylethyl) cysteine", *J. Biol. Chem.*, 245(18):3868–3871 (1970).

Furst, P., et al., "Cooper Activates Metallothionein Gene Transcription by Altering the Conformation of a Specific DNA Binding Protein", *Cell*, 55:705–717 (1988).

Han, J.H., et al., "Cloning and Expression of cDNA Encoding Antistasin, A Leech–derived Protein Having Anti–coagulant and Anti–metastatic Properties", *Gene*, 75:47–57 (1989).

Hinnen, A., et al., "Transformation of Yeast", *PNAS*, 73(4):1929–1933 (1978).

Holstein, T.W., et al., The Primitive Metazoan Hydra Expresses Antistasin, A Serine Protease Inhibitor of Vertebrate Blood Coagulation: cDNA Cloning, Cellular Localisation and Developmental Regulation:, *FEBS Letters*, 309(3):288–292 (1992).

(List continued on next page.)

*Primary Examiner*—Elizabeth C. Kemmerer
*Assistant Examiner*—Brian Lathrop
*Attorney, Agent, or Firm*—Myra H. McCormack

[57] ABSTRACT

The present invention relates to novel inhibitors belonging to the family of antistasin-type serine proteinase inhibitors, to their isolation from the medical leech *Hirudo medicinalis*, to DNA sequences encoding the novel inhibitors, to variants obtained by recombinant DNA technology or peptide synthesis, pharmaceutical compositions containing the inhibitors, and to their use in diagnosis and therapy.

15 Claims, 1 Drawing Sheet

OTHER PUBLICATIONS

Morrison, J.F., "Kinetics of the Reversible Inhibition of Enzyme–catalysed Reactions by Tight–Binding Inhibitors", *Biochim. Biophys. Acta*, 185:269–286 (1969).

Nutt, Elka, et al., "The Amino Acid Sequence of Antistasin—A Potent Inhibitor of Factor Xa Reveals a Repeated Internal Structure", *J. Biol. Chem.*, 263(21):10162–10167 (1988).

Harvey, R.P., et al., "Cloning and Expression of a cDNA coding for the anticoagulant Hirudin from the Bloodsucking Leech, *Hirudo medicinalis*", *PNAS*, 83(2):1084–1088 (1986).

Rudolph, H., et al., "One–step Gene Replacement in Yeast by Cotransformation", *Gene*, 36:87–95 (1985).

Smith, P.K., et al., "Measurement of Protein Using Bicinchoninic Acid", *Analytical Biochemistry*, 150:76–85 (1985).

Tuszynski, G.P., et al., Isolation and Characterization of Antistasin—An Inhibitor of Metastasis and Coagulation:, *J. Biol. Chem.*, 262(20):9718–9723 (1987).

Vlasuk, G.P., et al., Comparison of the In Vivo Anticoagulant Properties of Standard Heparin and the Highly Selective Factor Xa Inhibitors Antistasin and Tick Anticoagulant Peptide (TAP) in a Rabbit Model of Venous Thrombosis:, *Thrombosis Haemostasis*, 65:257–262 (1991).

Zhou, G.X., Kallistatin: A Novel Human Tissue Kallikrein Inhibitor, *J. Biol. Chem.*, 267(36):25873–25880 (1992).

Zoller, M.J., et al., Oligonucleotide–Directed Mutagenesis of DNA Fragments Cloned into M13 Vectors:, *Methods in Enzymology, vol. 100*, Part B., Chapter 32:468–500, published by Academic Press (1983).

SEQUENCE LISTING ( 1 ) GENERAL INFORMATION:

( i i i ) NUMBER OF SEQUENCES: 20

( 2 ) INFORMATION FOR SEQ ID NO: 1:

( i ) SEQUENCE CHARACTERISTICS:
        ( A ) LENGTH: 55 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..55
        ( D ) OTHER INFORMATION: /label= hirustasin ( x i ) SEQUENCE DESCRIPTION: SEQ ID NO: 1:

```
Thr Gln Gly Asn Thr Cys Gly Gly Glu Thr Cys Ser Ala Ala Gln Val
 1               5                  10                  15

Cys Leu Lys Gly Lys Cys Val Cys Asn Glu Val His Cys Arg Ile Arg
                20                  25                  30

Cys Lys Tyr Gly Leu Lys Lys Asp Glu Asn Gly Cys Glu Tyr Pro Cys
                35                  40                  45

Ser Cys Ala Lys Ala Ser Gln
                50                  55
```

( 2 ) INFORMATION FOR SEQ ID NO: 2:

( i ) SEQUENCE CHARACTERISTICS:
        ( A ) LENGTH: 1114 base pairs
        ( B ) TYPE: nucleic acid
        ( C ) STRANDEDNESS: single
        ( D ) TOPOLOGY: linear (  i  i  ) MOLECULE TYPE: DNA (genomic)

(  i  x  ) FEATURE:
  ( A ) NAME/KEY: misc_feature
  ( B ) LOCATION: 1110..1114
  ( D ) OTHER INFORMATION: /function= "BamHI site"

(  i  x  ) FEATURE:
  ( A ) NAME/KEY: misc_feature
  ( B ) LOCATION: 639..647
  ( D ) OTHER INFORMATION: /function= "BglII site"

(  i  x  ) FEATURE:
  ( A ) NAME/KEY: promoter
  ( B ) LOCATION: 1..403
  ( D ) OTHER INFORMATION: /function= "GAPDH promoter"

(  i  x  ) FEATURE:
  ( A ) NAME/KEY: sig_peptide
  ( B ) LOCATION: 404..658
  ( D ) OTHER INFORMATION: /function= "alpha-factor signal peptide"

(  i  x  ) FEATURE:
  ( A ) NAME/KEY: mat_peptide
  ( B ) LOCATION: 659..823
  ( D ) OTHER INFORMATION: /product= "hirustasin"

(  i  x  ) FEATURE:
  ( A ) NAME/KEY: terminator
  ( B ) LOCATION: 826..1109
  ( D ) OTHER INFORMATION: /standard_name= "alpha-factor terminator"

( x i ) SEQUENCE DESCRIPTION: SEQ ID NO: 2:

```
GATCCCCAGC  TTAGTTCATA  GGTCCATTCT  CTTAGCGCAA  CTACAGAGAA  CAGGGGCACA    60
AACAGGCAAA  AAACGGGCAC  AACCTCAATG  GAGTGATGCA  ACCTGCCTGG  AGTAAATGAT   120
GACACAAGGC  AATTGACCCA  CGCATGTATC  TATCTCATTT  TCTTACACCT  TCTATTACCT   180
TCTGCTCTCT  CTGATTTGGA  AAAAGCTGAA  AAAAAAGGTT  GAAACCAGTT  CCCTGAAATT   240
ATTCCCCTAC  TTGACTAATA  AGTATATAAA  GACGGTAGGT  ATTGATTGTA  ATTCTGTAAA   300
TCTATTTCTT  AAACTTCTTA  AATTCTACTT  TTATAGTTAG  TCTTTTTTTT  AGTTTTAAAA   360
CACCAAGAAC  TTAGTTTCGA  ATAAACACAC  ATAAGAATTC  AAAATGAGAT  TTCCTTCAAT   420
TTTTACTGCA  GTTTTATTCG  CAGCATCCTC  CGCATTAGCT  GCTCCAGTCA  ACACTACAAC   480
AGAAGATGAA  ACGGCACAAA  TTCCGGCTGA  AGCTGTCATC  GGTTACTTAG  ATTTAGAAGG   540
GGATTTCGAT  GTTGCTGTTT  TGCCATTTTC  CAACAGCACA  AATAACGGGT  TATTGTTTAT   600
AAATACTACT  ATTGCCAGCA  TTGCTGCTAA  AGAAGAAGAG  ATCTTGCTGG  ATAAAAGAAC   660
CCAAGGTAAC  ACCTGTGGTG  GTGAAACCTG  TTCTGCCGCC  CAAGTTTGTT  TGAAGGGTAA   720
GTGTGTTTGT  AACGAAGTTC  ACTGTCGTAT  TCGTTGTAAG  TACGGTTTGA  AGAAGGACGA   780
AAACGGTTGT  GAATACCCAT  GTTCTTGTGC  CAAGGCTCT   CAATGAGTCG  ACTTGTTCC    840
CACTGTACTT  TTAGCTCGTA  CAAAATACAA  TATACTTTTC  ATTTCTCCGT  AAACAACATG   900
TTTTCCCATG  TAATATCCTT  TTCTATTTTT  CGTTCCGTTA  CCAACTTTAC  ACATACTTTA   960
TATAGCTATT  CACTTCTATA  CACTAAAAAA  CTAAGACAAT  TTTAATTTTG  CTGCCTGCCA  1020
TATTTCAATT  TGTTATAAAT  TCCTATAATT  TATCCTATTA  GTAGCTAAAA  AAAGATGAAT  1080
GTGAATCGAA  TCCTAAGAGA  ATTAATTCGG  ATCC                                1114
```

( 2 ) INFORMATION FOR SEQ ID NO: 3:

(  i  ) SEQUENCE CHARACTERISTICS:
    ( A ) LENGTH: 1154 base pairs ( B ) TYPE: nucleic acid
            ( C ) STRANDEDNESS: single
            ( D ) TOPOLOGY: linear ( i i ) MOLECULE TYPE: DNA (genomic)

( i x ) FEATURE:
            ( A ) NAME/KEY: misc_feature
            ( B ) LOCATION: 435..439
            ( D ) OTHER INFORMATION: /function= "EcoRI site"

( i x ) FEATURE:
            ( A ) NAME/KEY: misc_feature
            ( B ) LOCATION: 679..687
            ( D ) OTHER INFORMATION: /function= "BglII site"

( i x ) FEATURE:
            ( A ) NAME/KEY: promoter
            ( B ) LOCATION: 1..443
            ( D ) OTHER INFORMATION: /function= "CUP1 promoter"

( i x ) FEATURE:
            ( A ) NAME/KEY: sig_peptide
            ( B ) LOCATION: 444..698
            ( D ) OTHER INFORMATION: /function= "alpha-factor siganl
                  sequence"

( i x ) FEATURE:
            ( A ) NAME/KEY: mat_peptide
            ( B ) LOCATION: 699..863
            ( D ) OTHER INFORMATION: /product= "hirustasin"

( i x ) FEATURE:
            ( A ) NAME/KEY: terminator
            ( B ) LOCATION: 867..1149
            ( D ) OTHER INFORMATION: /standard_name= "alpha-factor
                  terminator"

( i x ) FEATURE:
            ( A ) NAME/KEY: misc_feature
            ( B ) LOCATION: 1150..1154
            ( D ) OTHER INFORMATION: /function= "BamHI site"

( x i ) SEQUENCE DESCRIPTION: SEQ ID NO: 3:

| | | | | | |
|---|---|---|---|---|---|
| GATCCCCATT | ACCGACATTT | GGGCGCTATA | CGTGCATATG | TTCATGTATG | TATCTGTATT | 60 |
| TAAAACACTT | TTGTATTATT | TTTCCTCATA | TATGTGTATA | GGTTTATACG | GATGATTTAA | 120 |
| TTATTACTTC | ACCACCCTTT | ATTTCAGGCT | GATATCTTAG | CCTTGTTACT | AGTTAGAAAA | 180 |
| AGACATTTTT | GCTGTCAGTC | ACTGTCAAGA | GATTCTTTTG | CTGGCATTTC | TTCTAGAAGC | 240 |
| AAAAAGAGCG | ATGCGTCTTT | TCCGCTGAAC | CGTTCCAGCA | AAAAAGACTA | CCAACGCAAT | 300 |
| ATGGATTGTC | AGAATCATAT | AAAAGAGAAG | CAAATAACTC | CTTGTCTTGT | ATCAATTGCA | 360 |
| TTATAATATC | TTCTTGTTAG | TGCAATATCA | TATAGAAGTC | ATCGAAATAG | ATATTAAGAA | 420 |
| AAACAAACTG | TAACGAATTC | AAAATGAGAT | TTCCTTCAAT | TTTTACTGCA | GTTTTATTCG | 480 |
| CAGCATCCTC | CGCATTAGCT | GCTCCAGTCA | ACACTACAAC | AGAAGATGAA | ACGGCACAAA | 540 |
| TTCCGGCTGA | AGCTGTCATC | GGTTACTTAG | ATTTAGAAGG | GGATTTCGAT | GTTGCTGTTT | 600 |
| TGCCATTTTC | CAACAGCACA | AATAACGGGT | TATTGTTTAT | AAATACTACT | ATTGCCAGCA | 660 |
| TTGCTGCTAA | AGAAGAAGAG | ATCTTGCTGG | ATAAAAGAAC | CAAGGTAAC | ACCTGTGGTG | 720 |
| GTGAAACCTG | TTCTGCCGCC | CAAGTTTGTT | TGAAGGGTAA | GTGTGTTTGT | AACGAAGTTC | 780 |
| ACTGTCGTAT | TCGTTGTAAG | TACGGTTTGA | AGAAGGACGA | AAACGGTTGT | GAATACCCAT | 840 |
| GTTCTTGTGC | CAAGGCCTCT | CAATGAGTCG | ACTTTGTTCC | CACTGTACTT | TTAGCTCGTA | 900 |
| CAAAATACAA | TATACTTTTC | ATTTCTCCGT | AAACAACATG | TTTTCCCATG | TAATATCCTT | 960 |
| TTCTATTTTT | CGTTCCGTTA | CCAACTTTAC | ACATACTTTA | TATAGCTATT | CACTTCTATA | 1020 |
| CACTAAAAAA | CTAAGACAAT | TTTAATTTTG | CTGCCTGCCA | TATTTCAATT | TGTTATAAAT | 1080 |

TCCTATAATT TATCCTATTA GTAGCTAAAA AAAGATGAAT GTGAATCGAA TCCTAAGAGA        1140

ATTAATTCGG ATCC        1154

( 2 ) INFORMATION FOR SEQ ID NO: 4:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..42
        ( D ) OTHER INFORMATION: /function= "synthetic oligo for PCR"

( i x ) FEATURE:
        ( A ) NAME/KEY: misc_feature
        ( B ) LOCATION: 5..16
        ( D ) OTHER INFORMATION: /function= "synthetic sequence
            containing BamHI site"

( x i ) SEQUENCE DESCRIPTION: SEQ ID NO: 4:

GCATGGATCC CAGCTTAGTT CATAGGTCCA TTCTCTTAGC GC        42

( 2 ) INFORMATION FOR SEQ ID NO: 5:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..38
        ( D ) OTHER INFORMATION: /function= "synthetic oligo for PCR"

( x i ) SEQUENCE DESCRIPTION: SEQ ID NO: 5:

CTCGGAATTC TTATGTGTGT TTATTCGAAA CTAAGTTC        38

( 2 ) INFORMATION FOR SEQ ID NO: 6:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..41
        ( D ) OTHER INFORMATION: /function= "synthetic oligo for PCR"

( x i ) SEQUENCE DESCRIPTION: SEQ ID NO: 6:

GTGCGAATTC AAAATGAGAT TTCCTTCAAT TTTTACTGCA G        41

( 2 ) INFORMATION FOR SEQ ID NO: 7:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
    ( A ) NAME/KEY: misc_feature
    ( B ) LOCATION: 1..48
    ( D ) OTHER INFORMATION: /function= "synthetic oligo for PCR"

( x i ) SEQUENCE DESCRIPTION: SEQ ID NO: 7:

CAAAGTCGAC TTTATCCAGC AAGATCTCTT CTTCTTTAGC AGCAATGC 48

( 2 ) INFORMATION FOR SEQ ID NO: 8:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..50
        ( D ) OTHER INFORMATION: /function= "synthetic oligo for PCR"

( x i ) SEQUENCE DESCRIPTION: SEQ ID NO: 8:

GAAGAGATCT TGCTGGATAA AGTCGACTTT GTTCCCACTG TACTTTTAGC 50

( 2 ) INFORMATION FOR SEQ ID NO: 9:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..32
        ( D ) OTHER INFORMATION: /function= "synthetic oligo for PCR"

( x i ) SEQUENCE DESCRIPTION: SEQ ID NO: 9:

CCGGGGATCC GAATTAATTC TCTTAGGATT CG 32

( 2 ) INFORMATION FOR SEQ ID NO: 10:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..40
        ( D ) OTHER INFORMATION: /function= "synthetic oligo for PCR"

( x i ) SEQUENCE DESCRIPTION: SEQ ID NO: 10:

TAGAGGATCC CCATTACCGA CATTTGGGCG CTATACGTGC 40

( 2 ) INFORMATION FOR SEQ ID NO: 11:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
  ( A ) NAME/KEY: misc_feature
  ( B ) LOCATION: 1..39
  ( D ) OTHER INFORMATION: /function= "synthetic oligo for PCR"

( x i ) SEQUENCE DESCRIPTION: SEQ ID NO: 11:

```
CGACGAATTC ACAGTTTGTT TTTCTTAATA TCTATTTCG                                      39
```

( 2 ) INFORMATION FOR SEQ ID NO: 12:

( i ) SEQUENCE CHARACTERISTICS:
    ( A ) LENGTH: 90 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1..90
    ( D ) OTHER INFORMATION: /function= "synthetic oligo for PCR"

( x i ) SEQUENCE DESCRIPTION: SEQ ID NO: 12:

```
AAAGATCTTG CTGGATAAAA GAACCCAAGG TAACACCTGT GGTGGTGAAA CCTGTTCTGC              60
CGCCCAAGTT TGTTTGAAGG GTAAGTGTGT                                               90
```

( 2 ) INFORMATION FOR SEQ ID NO: 13:

( i ) SEQUENCE CHARACTERISTICS:
    ( A ) LENGTH: 90 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1..90
    ( D ) OTHER INFORMATION: /function= "synthetic oligo for PCR"

( x i ) SEQUENCE DESCRIPTION: SEQ ID NO: 13:

```
GTATTCACAA CCGTTTTCGT CCTTCTTCAA ACCGTACTTA CAACGAATAC GACAGTGAAC              60
TTCGTTACAA ACACACTTAC CCTTCAAACA                                               90
```

( 2 ) INFORMATION FOR SEQ ID NO: 14:

( i ) SEQUENCE CHARACTERISTICS:
    ( A ) LENGTH: 58 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: misc_feature
    ( B ) LOCATION: 1..58
    ( D ) OTHER INFORMATION: /function= "synthetic oligo for PCR"

( x i ) SEQUENCE DESCRIPTION: SEQ ID NO: 14:

```
TTGTCGACTC ATTGAGAGGC CTTGGCACAA GAACATGGGT ATTCACAACC GTTTTCGT                58
```

( 2 ) INFORMATION FOR SEQ ID NO: 15:

( i ) SEQUENCE CHARACTERISTICS:
    ( A ) LENGTH: 84 base pairs ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..84
        ( D ) OTHER INFORMATION: /function= "synthetic oligo for PCR"

( x i ) SEQUENCE DESCRIPTION: SEQ ID NO: 15:

AAGAATTCAT GCTTTTGCAA GCTTTCCTTT TCCTTTTGGC TGGTTTTGCA GCCAAAATAT    60

CTGCAACCCA AGGTAACACC TGTG    84

( 2 ) INFORMATION FOR SEQ ID NO: 16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..20
        ( D ) OTHER INFORMATION: /function= "synthetic oligo for PCR"

( x i ) SEQUENCE DESCRIPTION: SEQ ID NO: 16:

TTGTCGACTC ATTGAGAGGC    20

( 2 ) INFORMATION FOR SEQ ID NO: 17:

( i ) SEQUENCE CHARACTERISTICS:
        ( A ) LENGTH: 55 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..55
        ( D ) OTHER INFORMATION: /label= Antistatin Domain 1

( x i ) SEQUENCE DESCRIPTION: SEQ ID NO: 17:

Glu Gly Pro Phe Gly Pro Gly Cys Glu Glu Ala Gly Cys Pro Glu Gly
 1               5                  10                  15

Ser Ala Cys Asn Ile Ile Thr Asp Arg Cys Thr Cys Ser Gly Val Arg
            20                  25                  30

Cys Arg Val His Cys Pro His Gly Phe Gln Arg Ser Arg Tyr Gly Cys
            35                  40                  45

Glu Phe Cys Lys Cys Arg Lys
        50          55

( 2 ) INFORMATION FOR SEQ ID NO: 18:

( i ) SEQUENCE CHARACTERISTICS:
        ( A ) LENGTH: 63 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein (B) LOCATION: 1..63
        (D) OTHER INFORMATION: /label= Antistatin Domain 2

(xi) SEQUENCE DESCRIPTION: SEQ ID NO: 18:

Glu Pro Met Lys Ala Thr Cys Asp Ile Ser Glu Cys Pro Glu Gly Met
1               5                   10                  15

Met Cys Ser Arg Lys Thr Asn Lys Cys Asp Cys Lys Ile Asp Ile Asn
            20                  25                  30

Cys Arg Lys Thr Cys Pro Asn Gly Leu Lys Arg Asp Lys Gly Cys Glu
        35                  40                  45

Tyr Cys Glu Cys Arg Phe Lys Arg Lys Leu Ile Pro Arg Leu Ser
    50              55                  60

(2) INFORMATION FOR SEQ ID NO: 19:

(i) SEQUENCE CHARACTERISTICS:
        (A) LENGTH: 34 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..34
        (D) OTHER INFORMATION: /label= Hydra-Antistatin Domain 1

(xi) SEQUENCE DESCRIPTION: SEQ ID NO: 19:

Glu Cys Asn Lys Ile Gln Cys Arg Met Phe Cys Lys Phe Gly Phe Gln
1               5                   10                  15

Gln Asp Glu Asn Gly Cys Asp Ile Cys Lys Cys Ala Glu Arg Phe Glu
            20                  25                  30

Glu Lys (2) INFORMATION FOR SEQ ID NO: 20:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..32
        (D) OTHER INFORMATION: /function= "oligo"

(xi) SEQUENCE DESCRIPTION: SEQ ID NO: 20:

AATTCGGATC C                                                                      11

ANTISTASIN TYPE SERINE PROTEASE INHIBITORS

FIELD OF THE INVENTION

The present invention relates to novel inhibitors belonging to the family of antistasin-type serine proteinase inhibitors, to their isolation from the medical leech *Hirudo medicinalis*, to DNA sequences encoding the novel inhibitors, to variants obtained by recombinant DNA technology or peptide synthesis, pharmaceutical compositions containing the inhibitors, and to their use in diagnosis and therapy.

BACKGROUND OF THE INVENTION

Antistasin is a cysteine-rich serine proteinase inhibitor originally isolated from the salivary glands of the Mexican leech *Haementeria officinalis* (Tuszynski et al., J. Biol. Chem. (1987), 262, 9718–9723). Considerable interest has been focused on this polypeptide of 119 amino acids as it is a highly selective, tight binding inhibitor of the blood coagulation factor Xa and thus a potent anticoagulant in vitro and in vivo (Viasuk et al., Thromb. Haemostasis (1991), 65, 257–262). In addition, antistasin seems to have marked antimetastatic properties (Tuszynski et al., J. Biol. Chem. (1987), 262, 9718–9723).

Amino acid sequence analysis revealed that antistasin contains two homologous domains; no sequence similarity was found to other known proteins suggesting that antistasin is the prototype of a new family of serine proteinase inhibitors (Nutt et al., J. Biol. Chem. (1988), 263, 10162–10167). Meanwhile, only one protein related to antistasin has been identified: ghilanten, isolated from the giant Amazonian leech *Haementeria ghilianii* is nearly identical to antistasin with respect to amino acid sequence (>90% identity) and functional properties. Recently, a cDNA sequence containing a highly conserved 6-fold repeat with homology to the C-terminal halves of the antistasin-domains has been identified in Hydra (Holstein et al., FEBS Lett., (1992), 309, 288–292); however it, is unclear whether the putative protein encoded by this cDNA sequence has any activity as proteinase inhibitor or antimetastatic agent.

In the present invention novel members of the family of antistasin-type inhibitors are presented. These polypeptides, named hirustasin (Hirudo antistasin), have been isolated from the medical leech *Hirudo medicinalis*, and their amino acid sequence and characteristics as proteinase inhibitors have been determined. As illustrated in further detail below hirustasin and variants thereof obtained by recombinant DNA technology or peptide synthesis have therapeutic potential in disorders related to the action of serine proteinases such as trypsin, chymotrypsin, tissue kallikrein and cathepsin G, and as antimetastatic agents.

Although the putative reactive site residues of hirustasin and antistasin are nearly identical (FIG. 1), hirustasin neither affects the catalytic activity of isolated factor Xa nor the blood coagulation cascade in vitro.

DESCRIPTION OF THE INVENTION

The invention concerns to a polypeptide comprising the amino acid sequence as given in SEQ ID NO:1 (hirustasin) or a mutant, functional fragment or derivative thereof.

The expression mutant, functional fragment or derivative thereof includes all fragments or derivatives of said polypeptide that still bind to or inhibit serine proteinases, such as trypsin, chymotrypsin, tissue kallikrein and cathepsin G; or that act as antimetastatic agents. In a preferred embodiment the inventive polypeptide is used as anticoagulant.

Mutants are for example polypeptides having amino acids substituted or deleted at one or more positions.

The expression derivatives includes pharmaceutical acceptable salts with acids, like hydrohalic acids such as hydrochloric acid; sulfuric acid, phosphoric acid, pyrophosphoric acid, benzenesulfonic acid, p-toluenesulfonic acid, methanesulfonic acid, lactic acid, palmic acid, tartaric acid, ascorbic acid, citric acid; with bases like nitrogen-containing bases such as sodium, potassium, magnesium or ammonium nitrogen-containing bases; or inner salts.

Also included are modified forms of said polypeptides, e.g. polypeptides bearing a detectable marker, such as a fluorescent, chemiluminescent or radioactive marker or avidin, biotin or the like.

Fragments of said polypeptide embraces C- or N-terminal shortened fragments as well as fragments from within the polypeptide chain that bind to or inhibit serine proteinases, such as tissue kallikrein, cathepsin G, and factor Xa; or that act as antimetastatic agents. Embraced is for example a fragment wherein the C-terminal Gln is missing.

These fragments can be used alone or in combination with others such as other proteins (fusion proteins) or chemical compounds. Examples for combinations are, e.g., the combination of the binding domain of hirustasin with chemically synthesized inhibitors, e.g. to increase the stability against proteolysis; the combination of the inhibitory domain of hirustasin with the binding domain of a different polypeptide, e.g. to direct the action of the inhibitory domain to a different substrate or to increase the specificity of hirustasin; or the combination of hirustasin with another polypeptide or oligopeptide; e.g. to induce a specific uptake into a certain compartment.

The inventive polypeptides are obtained by peptide synthesis, or recombinant DNA technology or are isolated from a leech, especially form *Hirudo medicinalis*, by conventional methods, e.g., by a) obtaining an extract of a leech, preferable of the medical leech *Hirudo medicinalis*, and b) purifying the extract by dialysis and column chromatography, e.g. by cation exchange chromatography, biospecific affinity chromatography and/or a further ion exchange chromatography step.

An other embodiment of the invention is a recombinant DNA coding for the inventive polypeptide or a fragment of said DNA.

Fragments of said DNAs are for example coding for a functional domain of the inventive polypeptide or are suitable as hybridization probes in screening procedures. Hybridization probes for selective screening procedures are usually fragments of said nucleic acid comprising more than 15 nucleotides.

Expression cassettes

A further embodiment of the invention is a polypeptide expression cassette comprising a promoter operably linked to a DNA sequence coding for the inventive polypeptide as defined above and to a DNA sequence containing transcription termination signals.

In hosts capable of secreting expressed polypeptides, the expression cassette preferably comprises a promoter operably linked to a first DNA sequence encoding a signal peptide linked in the proper reading frame to a second DNA sequence coding for the inventive polypeptide, and a DNA sequence containing transcription termination signals.

In a preferred embodiment, the promoter, the signal sequence and the terminator are recognized by the yeast expression system.

Promoter suitable for expression in a certain host are well known. Examples are the promoter of the TRP1 gene, the ADHI or ADHII gene, acid phosphatase (PHO5) gene, CUP1 gene, isocytochrome c gene, or a promoter of the genes coding for glycolytic enzymes, such as TDH3, glyceraldehyde-3-phosphate dehydrogenase (GAPDH), a shortened version of GAPDH (GAPFL), 3-phosphoglycerate kinase (PGK), hexokinase, pyruvate decarboxylase, phosphofructokinase, glucose-6-phosphate isomerase, 3-phosphoglycerate mutase, pyruvate kinase, triosephosphate isomerase, phosphoglucose isomerase, invertase and glucokinase genes, or a promoter of the yeast mating pheromone genes coding for the a- or α-factor, can be used. Preferred vectors of the present invention contain, e.g., promoters with transcriptional control that can be turned on or off by variation of the growth conditions, e.g. the promoter of the PHO 5 or the CUP 1 gene. For example, the PHO 5 promoter can be repressed or derepressed at will, solely by increasing or decreasing the concentration of inorganic phosphate in the medium and the CUP1 promoter can be turned on by the addition of $Cu^{2+}$-ions to the medium, e.g., in the form of a copper salt. Especially preferred are the GAPDH and the yeast CUP1 promoter.

The DNA sequence encoding a signal peptide ("signal sequence"), e.g. a yeast signal peptide, is preferably derived from a gene, e.g. a yeast gene, coding for a polypeptide which is ordinarily secreted. Yeast signal sequences are, for example, the signal and prepro sequences of the yeast invertase (SUC2), α-factor, pheromone peptidase (KEX1), "killer toxin" and repressible acid phosphatase (PHO5) genes and the glucoamylase signal sequence from *Aspergillus awamori*. Additional sequences, such as pro- or spacer-sequences which may carry specific processing signals can also be included in the constructions to facilitate accurate processing of precursor molecules. For example, the processing signals contain a Lys-Arg residue, which is recognized by a yeast endo peptidase located in the Golgi membranes. The preferred signal sequences according to the present invention are those of the yeast PHO5 gene, the α-factor and of the yeast invertase gene (SUC2).

A DNA sequence containing transcription termination signals, e.g. yeast transcription termination signals, is preferably the 3' flanking sequence of a gene, e.g. a yeast gene, which contains proper signals for transcription termination and polyadenylation. The preferred flanking sequence is that of the yeast PHO5 and the α-factor gene.

The DNA coding for the polypeptide according to the invention may be isolated from a gene bank of the natural host (the medical leech *Hirudo medicinalis*) by methods known in the art or synthesized by PCR using, e.g., the preferred codon usage of the host.

The promoter, the DNA sequence coding for the signal peptide, the DNA sequence coding for the polypeptide and the DNA sequence containing transcription termination signals are operably linked to each other, i.e. they are juxtaposed in such a manner that their normal functions are maintained. The array is such that the promoter effects proper expression of the signal sequence-polypeptide gene complex, the transcription termination signals effect proper termination of transcription and polyadenylation and the signal sequence is linked in the proper reading frame to the polypeptide gene in such a manner that the last codon of the signal sequence is directly linked to the first codon of the gene for the polypeptide. The yeast promoter is preferably joined to the signal sequence between the major mRNA start and the ATG naturally linked to the promoter gene. The signal sequence has its own ATG for translation initiation. The junction of these sequences may, for example, be effected by means of synthetic oligodeoxynucleotide linkers carrying the recognition sequence of an endonuclease. Examples for related expression cassettes are described e.g. in EP-A-341215.

Preferred expression cassettes comprise the CUP1 or the GAPDH promoter, the α-factor or the yeast invertase leader sequence, the hirustasin gene and the α-factor terminator.

Especially preferred expression cassette comprise a recombinant DNA molecule as described in SEQ ID NO:2 or SEQ ID NO:3 or a functional fragment or derivative thereof.

Recombinant Plasmids

A further embodiment of the invention concerns a recombinant plasmid comprising a polypeptide expression cassette as described above.

Apart from the polypeptide expression cassette the expression plasmids according to the invention can comprise a DNA segment originating from two-micron DNA containing the origin of replication or, if a two-micron DNA free strain of yeast is used, total two-micron DNA. The latter type of plasmids is preferred. For example, the plasmids according to the invention contain the complete two-micron DNA in an uninterrupted form, i.e. two-micron DNA is cleaved once with a restriction endonuclease, the linearized DNA is linked with the other components of the vector prior to recircularization. The restriction site is chosen such that to recircularization. The restriction site is chosen such that normal function of the REP1, REP2 and FLP genes and of the ORI, STB, IR1 and IR2 sites of two-micron DNA as well as small "FLP recognition target" (FRT) sites, located near the center of each inverted repeat (IR) at which the FLP recombinase acts, is maintained. Optionally, the restriction site is chosen such that the D gene of two-micron DNA is kept intact too. Suitable restriction sites are, for example, the unique PstI site located within the D gene and the unique HpaI and SnaBI sites located outside of all of said genes and sites. However, it is likewise possible to insert the expression cassette and further components (cf. below) at different (such as two) restriction sites, especially those mentioned above, within two-micron DNA.

Such a plasmid derivative may comprise two invertedly repeated FRT sites or an additional, third FRT site. The former kind of plasmid is hereinafter called a "symmetric two micron-like hybrid vector". The latter kind of plasmid is hereinafter called "symmetric two micron-like disintegration vector" despite it is not a real symmetric plasmid but gives rise to a symmetric two micron-like hybrid vector in the yeast cell transformed therewith.

A symmetric two micron-like hybrid vector of the invention does preferentially not contain bacterial or viral DNA sequences, i.e. DNA derived from a bacterial genome, plasmid or virus. However, a two micron-like disintegration vector of the invention may comprise DNA sequences of prokaryotic origin between the two directly repeated FRT sites which are excised from the vector in the transformed yeast cell in which the symmetric two micron-like hybrid vector is generated from the disintegration vector. These DNA sequences are bacterial sequences as described below and can provide to the vector essential structural or functional features or can also only have the function of filling up the two regions between the two invertedly repeated FRT sites of an unsymmetric two micron-like plasmid derivative or of an "unsymmetric" disintegration vector in order to construct a symmetric two micron-like hybrid vector or a symmetric disintegration vector.

In a two micron-like hybrid vector which is symmetric within the meaning of the present invention or in a disintegration vector which gives rise to such a symmetric two micron-like hybrid vector the lengths of the regions located between the two invertedly repeated FRT sites have a ratio from about 1:1 up to about 5:4, i.e. the larger region is up to about 20% larger than the smaller one.

In one preferred embodiment of invention, the two regions between invertedly repeated FRT sites of the circular form of the two-micron DNA have approximately the same length.

Preferably, the expression plasmids according to the invention include one or more, especially one or two, selective genetic markers, e.g. a marker for yeast and a marker and (except for symmetric two-micron like hybrid vectors) an origin of replication for a bacterial host, especially *Escherichia coli*.

As to the selective gene markers, any marker gene can be used which facilitates the selection for transformants due to the phenotypic expression of the marker gene. Suitable markers are, for example, those expressing antibiotic resistance or, in the case of auxotrophic yeast mutants, genes which complement host lesions. Corresponding genes confer, for example, resistance to the antibiotics G418, hygromycin or bleomycin or provide for prototrophy in an auxotrophic yeast mutant, for example the URA 3, LEU 2, LYS 2, HIS 3 or TRP 1 gene.

As the amplification of the expression plasmids is conveniently done in a prokaryote, such as *E. coli*, a prokaryote, e.g. *E. coli*, genetic marker and a prokaryote, e.g. *E. coli*, replication origin are included advantageously. These can be obtained from corresponding prokaryotic plasmids, for example *E. coli* plasmids, such as pBR322 or a pUC plasmid, for example pUC18 or pUC19, which contain both prokaryotic, e.g. *E. coli*, replication origin and genetic marker conferring resistance to antibiotics, such as ampicillin.

Apart from the polypeptide expression cassette, replication origin(s) and genetic marker(s) the expression plasmids according to the invention can contain optionally additional expression cassettes, such as 1 to 3 additional polypeptide expression cassettes and/or one additional transcriptional activator ACE1 expression cassette. The additional polypeptide expression cassette(s) are identical to or different from each other and are identical to or different from the polypeptide expression cassette already present on the vector and each comprise a suitable promoter operably linked to a first DNA sequence encoding a signal peptide linked in the proper reading frame to a second DNA sequence encoding the polypeptide and a DNA sequence containing suitable transcription termination signals. A suitable yeast promoter in such an additional polypeptide-expression cassette is, for example, any constitutive or inducible yeast promoter which can be used for the expression of polypeptides by yeast in complex media, as described above. Suitable signal sequences and transcription termination signals are especially those described above. An additional ACE1 expression cassette includes its own transcriptional and translational initiation and termination signals or, in the alternative, is transcriptionally controlled by a constitutive or inducible yeast promoter different from the ACE1 promoter, such as the CUP1 or a constitutive (shortened) GAPDH promoter (e.g. GAPFL promoter). A suitable ACE1 expression cassette is, for example, contained in the *S. cerevisiae* genomic 1.7 kb EcoRV fragment (Fürst et al., Cell (1988), 55, 705–717). The genuine ACE1 promoter therein can be replaced by another yeast promoter, e.g. the CUP1 promoter, by conventional means and methods. The direction of transcription of the additional polypeptide and/or ACE expression cassettes is not crucial and may be the same as or opposite to the direction of transcription of the polypeptide-expression cassette already present in the vectors of the invention.

Hosts

A further embodiment of the invention concerns a host which contains hybrid plasmid as described above.

Suitable hosts are of prokaryotic or eukaryotic origin. Examples are microbiological hosts like bacterial, fungal, plant or insect cells. Preferred hosts are bacterial and fungal cells such as *E. coli* or fungi like *Saccharomyces cerevisiae*, *Aspergillus niger*, *Aspergillus nidulans* or *Neurospora crassa*.

Preferred yeast strains are those mentioned above, e.g. strains of *S. cerevisiae* which have been cured of the endogenous two-micron plasmid ("cir$^0$ strains") and especially strains which are singly or multiply deficient in yeast proteases; and/or, in the case the CUP1 promoter is used, yeast strains containing 1–3 additional copies of the chromosomal ACE1 gene.

A wide variety of proteinases, like those mentioned, have been characterized in the yeast *Saccharomyces cerevisiae* (Achstetter et al., Yeast (1985), 1, 139–157). Mutants lacking activity of most of these proteases have been isolated and studied biochemically. The consequences of the absence of certain proteases were elucidated and some properties proved to be useful for the production of heterogeneous proteins. The proteases which are lacking in the yeast strains according to the invention do not perform indispensable functions in the cell metabolism; therefore mutations which completely destroy the activity of these proteins are not lethal. For example, the yeast strain lack one or more proteases selected from the group of carboxypeptidases yscα, yscB, yscA, yscY and yscS.

Methods for the production of such yeast strains are described, for example, in EP-A-340170 and EP-A-341215. Yeast strains deficient in genomic CUP1 gene product activity are known or can be prepared in a manner known per se, for example by site-directed mutagenesis or gene-disruption or gene replacement (Rudolph et al., Gene (1985), 36, 87–95). In case the sequence of the gene to be inactivated is known, the latter can be made defective by insertion, substitution or deletion making use of the well-known site directed mutagenesis procedure (see, for example, M. J. Zoller and M. Smith Methods Enzymol. (1983), 100, 468) which involves the preparation of an appropriately devised mutagenic oligodeoxyribonucleotide primer. The gene replacement or directed mutagenesis procedures are commonly applied in the art and are absolutely reproducible.

A further current method to create yeast strains having a desired genetic background, for example having chromosomal CUP1 genes disrupted and/or having deficiencies in certain proteases, consists in meiotic crossing of suitable yeast strains and subsequent tetrad analysis. The tetrads, which derive from the diploid cells, are dissected according to standard genetic techniques. Random assortment among the four spores of a tetrad allows the construction of suitable mutants in subsequent crosses. Random spore analysis can also be used as an alternative system.

Yeast strains containing 1–3 additional copies of the chromosomal ACE1 gene can also be prepared in a conventional manner. For example, the ACE1 gene(s) can be inserted into appropriate restriction site(s) of chromosomal gene(s) conferring antibiotic resistance or in gene(s) involved in amino acid or purine or pyrimidine base synthesis rendering resulting yeast strains containing such additional copy (copies) of the ACE1 gene antibiotic sensitive and, respectively, auxotrophic with respect to the corresponding amino acid, purine or pyrimidine base.

The transformation of host with the hybrid plasmids according to the invention may be accomplished according to methods known in the art.

Process for the production of polypeptides

A further part of the invention is a process for the production of hirustasin or a functional fragment or derivative thereof, as described above, comprising culturing a host, as described above, transformed with an polypeptide expression cassette, as described above, and isolating the protein produced thereby.

The polypeptide can be isolated by conventional means. For example, the first step consists usually in lysing the cell wall and removing the cell debris by centrifugation or, in the case of secretory proteins, in separating the cells from the culture fluid by means of centrifugation. The resulting supernatant can be enriched for polypeptide by treatment with polyethyleneimine so as to remove most of the non-proteinaceous material, and precipitation of the proteins by saturating the solution with ammonium sulfate. Host proteins, if present, can also be precipitated, for example, by means of acidification with acetic acid (for example 0.1%, pH 4–5). Other purification steps include, for example, desalination, chromatographic processes, such as ion exchange chromatography, gel filtration chromatography, partition chromatography, HPLC, reversed phase HPLC and the like. The separation of the constituents of the mixture is also effected by dialysis, according to charge by means of gel electrophoresis or carrier-free electrophoresis, according to molecular size by means of a suitable Sephadex® column, by affinity chromatography, for example with antibodies, especially monoclonal antibodies.

In the case of hirustasin, irrespective of the yeast strain, promoter and signal peptide used, the produced hirustasin is predominantly secreted into the culture medium and can be isolated therefrom. After centrifugation, trypsin, chymotrypsin or cathepsin G, coupled to a suitable carrier for affinity chromatography can be used to separate the hirustasin as well as other processes, especially those known from the literature.

Also enclosed is the production of a polypeptide as described above by chemical synthesis, e.g. in the form of solid phase synthesis (Merrifield synthesis).

Pharmaceutical compositions

Hirustatin (including mutants, functional fragments or derivatives thereof) obtainable in accordance with the present invention has valuable pharmacological properties and can be used prophylactically or therapeutically for the treatment of the human or animal body. Therapeutic treatment of the human or animal body is particularly suitable in the present invention.

The inventive polypeptides are potent inhibitors of serine proteinases such as trypsin, chymotrypsin, tissue kallikrein and cathepsin G, and can be used, e.g., as antimetastatic agents. They have, for example, a $K_i$ value of $10^{-9}$M to $10^{-13}$M.

These polypeptides are for example completely specific to tissue kallikrein and exhibit no interactions with other proteinases of the blood coagulation system and therefore can be used as specific kallikrein inhibitors.

The novel polypeptides according to the invention can therefore be used for the therapy and prophylaxis of thromboses and thromboembolisms, including the prophylaxis of postoperative thromboses, for acute shock therapy (for example for septic or polytraumatic shock), for the therapy of consumption coagulopathies, in haemodialyses, haemoseparations and in extracorporeal blood circulation.

Kallikrein is also involved in the pathophysiological process of maintenance of systemic blood pressure. The inventive polypeptides can therefore be used also in the management of hypertension.

The invention relates also to pharmaceutical compositions that contain a therapeutically effective amount of at least one of the polypeptides according to the invention or a pharmaceutically acceptable salt thereof, optionally together with a pharmaceutically acceptable carrier and/or adjuncts.

These compositions can be used especially in the above-mentioned indications, when they are administered, for example, parenterally, such as intravenously, intracutaneously, subcutaneously or intramuscularly, optionally together with conventional carriers.

The invention relates also to the use of the novel polypeptides according to the invention and to pharmaceutical compositions containing them for the prophylactic and therapeutic treatment of the human or animal body, especially for the above-mentioned clinical syndromes.

The dosage depends especially on the specific form of administration and on the purpose of the therapy or prophylaxis. The size of the individual doses and the administration regime can best be determined by way of an individual judgment of the particular case of illness; the methods of determining relevant blood factors required for this purpose are familiar to the person skilled in the art. Normally, in the case of an injection the therapeutically effective amount of the polypeptides according to the invention is in a dosage range of from approximately 0.005 to approximately 0.1 mg/kg body weight. A range of from approximately 0.01 to approximately 0.05 mg/kg body weight is preferred. The administration is effected by intravenous, intramuscular or subcutaneous injection. Accordingly, pharmaceutical compositions for parenteral administration in single dose form contain per dose, depending on the mode of administration, from approximately 0.4 to approximately 7.5 mg of the polypeptide according to the invention. In addition to the active ingredient these pharmaceutical compositions usually also contain a buffer, for example a phosphate buffer, which is intended to keep the pH value between approximately 3.5 and 7, and also sodium chloride, mannitol or sorbitol for adjusting the isotonicity. They may be in freeze-dried or dissolved form, it being possible for solutions advantageously to contain an antibacterially active preservative, for example from 0.2 to 0.3% 4-hydroxybenzoic acid methyl ester or ethyl ester.

In addition to the compositions described above that are intended for direct medicinal use in the body of a human or an animal, the present invention relates also to pharmaceutical compositions for medicinal use outside the living body of humans or animals. Such compositions, such as stock solutions or alternatively compositions in single dose form, are similar in composition to the injection compositions described above; however, the amount or concentration of active ingredient is advantageously based on the volume of blood to be treated. Depending on the specific purpose, the suitable dose is from approximately 0.01 to approximately 1.0 mg of the active ingredient/liter of blood, although the upper limit may still be exceeded without risk.

BRIEF DESCRIPTION OF THE DRAWINGS

In the following experimental part various embodiments of the present invention are described with reference to the accompanying drawings in which.

Figure 1:
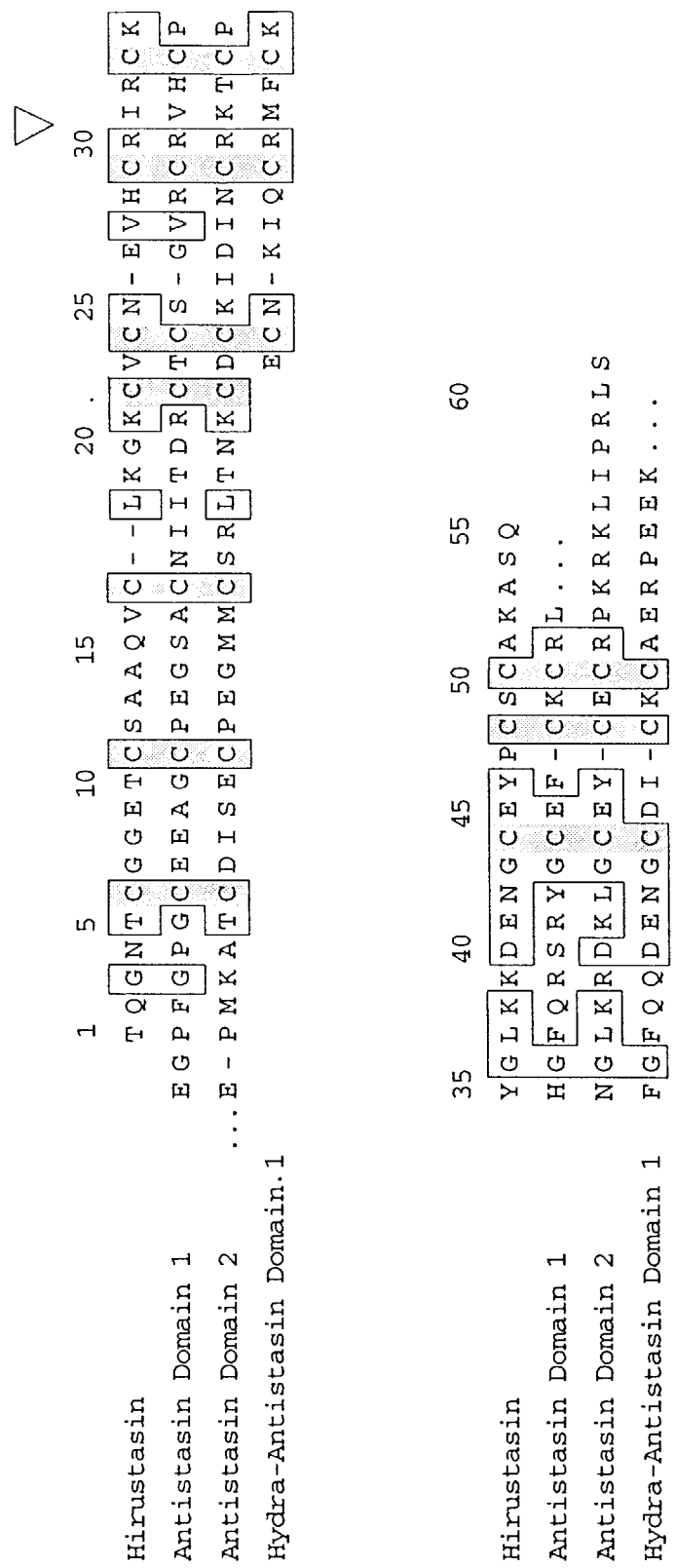
FIG. 1: Amino acid sequences of antistasin-type inhibitors. The sequences of hirustasin (SEQ. ID. NO: 12), both domains of antistasin (SEQ. ID. NO:17 and SEQ. ID. NO:18) (Nutt et al., J. Biol. Chem. (1988), 263, 10162–10167), and of the first of the 6 repeats of Hydra-antistasin (SEQ. ID. NO.:19) (Holstein et al., FEBS Lett., (1992), 309, 288–292) are aligned. Identical amino acid residues are boxed, and cysteins are indicated by shadowing. The arrow marks the scissile peptide bond of antistasin (domain 1) and hirustasin.

EXAMPLES a) Inhibitory activity:

During the purification procedure inhibitory activity is assayed by measuring the inhibition of the amidolytic activities of trypsin and chymotrypsin. Samples are incubated with trypsin (225 nM) in 50 mM Tris/HCl (pH 7.8), 0.1% (mass/vol) Triton X-100, for 12 min at 25° C. The assay is started by addition of the substrate benzoyl-L-argininep-nitroanilide (0.4 mM, final concentration). The released nitroaniline is monitored photometrically at 405 nm for 3.5 min using an UVIKON 930® photometer (Kontron; Eching, Germany).

Similarly, inhibition of chymotrypsin (1.3 mM) is determined in a buffer containing 100 mM Tris/HCl, pH 7.8, 0.1% (mass/vol) Triton X-100, with Ac-L-tyrosine p-nitroanilide as substrate (0.7 mM, final concentration).

One inhibition unit (IU) is defined as the amount of inhibitor which reduces the substrate hydrolysis by 1 mmol per min.

b) Protein assay:

Protein concentrations are determined using the bicinchoninic acid procedure (Smith et. al., Anal. Biochem. (1985), 150, 76–85) with bovine serum albumin as standard.

c) DNA manipulations:

All DNA manipulations are—if not otherwise noted—carried out according to standard protocols (e.g. Sambrook et al., Molecular Cloning: A laboratory manual, $2^{nd}$ Edn. (1989))

Example 1

Purification of Hirustasin

Extracts from the medical leech *Hirudo medicinalis* are prepared as described in WO 86/03493 by extracting homogenized leeches with acetone and precipitation of impurities by successive addition of ethanol. The resolution solution is concentrated under vacuo and after fractionated precipitation with acetone, the precipitation received at highest acetone concentration is extracted with water and lyophilized.

a) Chromatography on SP-Sephadex®:

Lyophilized leech extract (~3.5 g) is dissolved in deionized water (77 ml) and dialyzed against 20 mM sodium phosphate (pH 8.0) over night at 4° C. The dialyzed material is applied onto a SP-Sephadex® column (1.6×20 cm) equilibrated with the same buffer. The column is washed until the optical density (280 nm) of the effluent reached baseline values, and eluted with 20 mM sodium phosphate buffer containing 500 mM NaCl (pH 8.0) at a flow rate of 1 ml/min. Fractions containing inhibitory active material are pooled.

b) Affinity-chromatography on anhydrotrypsin-Sepharose®:

Anhydrotrypsin is prepared from trypsin as described by Ako et al. (Ako et al., Biochem. Biophys. Res. Comm. (1972), 47, 1042–1047). It is immobilized onto cyanogen bromide-activated Sepharose 4B® (Pharmacia) according to the guidelines of Pharmacia.

The pooled material from the cation exchange chromatography (~20 ml) is applied onto an anhydrotrypsin-Sepharose® column (1.6×3.6 cm) equilibrated with 20 mM sodium phosphate buffer (pH 8.0). Approximately 50% of the inhibitory active material applied is bound; the remainder in the flow-through is collected for rechromatography. After extensive washing of the column (~10 column volumes) elution is started by addition of 100 mM KCl/HCl (pH 2.1) at a flow rate of 0.3 ml/min. Fractions are collected and neutralized immediately by addition of 1M Tris. The pooled eluates are dialyzed against 20 mM sodium phosphate (pH 8.0) over night at 4° C.

c) Chromatography on Mono S®:

The dialyzed eluate from the affinity chromatography is applied onto a Mono S® cation exchange column (0.5×5 cm, Pharmacia) equilibrated with 20 mM sodium phosphate (pH 8.0). The column is washed with the same buffer, and then eluted using a linear gradient from 60 to 120 mM NaCl at a flow rate of 1 ml/min. The elution profile of this final chromatography step reveals that the trypsin and chymotrypsin inhibitory activities co-elute with the major protein peak at ~100 mM NaCl. Fractions containing inhibitory active material are pooled (~6 ml), aliquoted, and stored at −20° C.

The results of a representative purification of hirustasin are summarized in Table 1.

TABLE 1

| Isolation step | Protein [mg] | Trypsin | | | | Chymotrypsin | | | |
|---|---|---|---|---|---|---|---|---|---|
| | | Inhibit. [IU] | SA [IU/mg] | Yield [%] | Purification | Inhibit. [IU] | SA [IU/mg] | Yield [%] | Purification |
| Leech extract | 2310 | 1090 | 0.47 | | | 36.7 | 0.016 | | |
| SP Sephadex ® | 36 | 9.4 | 0.27 | 100 | 65x | 0.52 | 0.015 | 100 | 65x |
| Anhydrotrypsin | 2.1 | 5.6 | 2.7 | 59 | 660x | 0.21 | 0.100 | 40 | 450x |
| Mono S ® | 0.96 | 2.6 | 2.7 | 28 | 680x | 0.14 | 0.15 | 27 | 650x |

IU = Amount of inhibitor which reduces the substrate hydrolysis by 1 mmol per min.
SA = Specific activity
* = with regard to protein The isolated hirustasin is homogeneous according to SDS-PAGE (10–20% polyacrylamide) which show a single band migrating somewhat slower than bovine pancreatic trypsin inhibitor after silver staining. Similarly, reversed phase HPLC and N-terminal sequence analysis suggest a purity of >90%.

Conditions for HPLC:

Samples (~1 nmol protein) are loaded onto a Lichrospher RP8® reversed phase column (125×4 mm; Merck) and eluted using a linear gradient from 0% to 40% (by volume) acetonitrile in 0.1% (by volume) trifluoroacetic acid within 40 min at a flow rate of 1 ml/min.

Two species of the inhibitor with an apparent $M_r$ of 5738 and 5866 are detected by mass spectroscopy. These $M_r$ values are in good agreement with those calculated from the amino acid sequence (see example 2) of hirustasin and of an inhibitor form truncated C-terminally by one amino acid ($M_r$ 5741 and 5869, respectively, assuming 5 disulfide bonds).

Conditions for mass spectroscopy:

The HPLC-purified inhibitor is infused into an atmospheric pressure ionization source fitted to a tandem quadrupole instrument API III (Sciex, Thornhill, Ontario, Canada) using a syringe infusion pump. The instrument is calibrated with the ammonium adduct ions of polypropylene glycol. The average molecular mass value of the protein was calculated from the m/z peaks in the charge distribution profiles of the multiple charged ions.

Example 2

Amino Acid Composition of Hirustasin

Amino acid analysis:

Samples of oxidized inhibitor are hydrolyzed under vacuum in 5.7M hydrochloric acid at 110° C. for 20 h and analyzed on a Biotronik LC 5000 high performance analyzer system (Puchheim, Germany). The results are shown in Table 2.

TABLE 2

| Amino acid | Residues/molecule determined by amino acid analysis | sequencing |
|---|---|---|
| Asx | 3.91 | 4 |
| Thr | 2.97 | 3 |
| Ser | 3.03 | 3 |
| Glx | 6.55 | 6/7[1] |
| Gly | 6.33 | 6 |
| Ala | 4.23 | 4 |
| Cys | 7.50 | 10 |
| Val | 2.67 | 3 |
| Ile | 1.16 | 1 |
| Leu | 2.05 | 2 |
| Tyr | 1.19 | 2 |
| His | 1.14 | 1 |
| Lys | 6.17 | 6 |
| Arg | 1.95 | 2 |
| Pro | 0.92 | 1 |
| Total | 51.8 | 54/55[1] |

[1]= Mass spectroscopy suggests the presence of two forms of hirustasin differing by a C-terminal glutamine.

a) Reduction and S-β-pyridylethylation:

S-β-pyridylethylation is carried out essentially as described by Friedman et al. (Friedman et al., J. Biol. Chem. (1970), 245, 3868–3871). The inhibitor (~1 nmol) is dissolved in 100 ml buffer (6M guanidinium-HCl, 0.25M Tris/HCl, 1 mM EDTA, 5% (vol/vol) β-mercaptoethanol; pH 8.5) and incubated overnight at room temperature. After addition of 5 ml 4-vinylpyridine and incubation for 90 min, the reaction is stopped by acidification with formic acid. The S-pyridylethylated inhibitor was desalted by reversed phase chromatography on an Aquapore RP 300® column (2.1×30 mm; Applied Biosystems, Weiterstadt, Germany).

b) Oxidation of the inhibitor:

A mixture of formic acid (100% by vol; 45 ml) and hydrogen peroxide (30% by vol; 5 ml) is preincubated for 1 h at RT. Thereafter, the inhibitor (~1 nmol) is added. After incubation for 1 h at 4° C., the reaction is stopped by dilution with 1 ml deionized water and lyophylization.

The N-terminal 21 amino acid residues of hirustasin are determined by automated Edman degradation (gas-phase sequencer 473A Applied Biosystems) of the native inhibitor (SEQ ID NO:1). Additional sequence information is obtained after fragmentation of the native and of the reduced and S-pyridylethylated inhibitor with trypsin and chymotrypsin.

The inhibitor (~1 nmol) is incubated with trypsin, chymotrypsin, or endoproteinase Glu-C (sequencing grade; Boehringer Mannheim) in 100 ml of 1M ammoniumhydrogen carbonate buffer (pH 8.0) for 14 h at 37° C. An enzyme/inhibitor ratio (mass/mass) of 1:40 is used for trypsin and chymotrypsin, and of 1:20 for endoproteinase Glu-C. The reactions are terminated by acidification with formic acid, the fragments resulting are separated by HPLC (as described above), and the major peptides are sequenced. Finally, to obtain fragments overlapping with the peptides Cys22-Arg30 and Ile31-Pro47, and to generate an additional C-terminal peptide, the inhibitor is digested with endoproteinase Glu-C. The complete structure of hirustasin and of the larger fragments sequenced is shown in SEQ ID NO:1. The sequence obtained is in good agreement with the result of the amino acid analysis (Tab. 2).

Example 3

Specificity of Hirustasin

The concentration of reactive sites determined by titration of the isolated protein with trypsin and chymotrypsin is identical. For this titration bovine pancreatic trypsin is standardized by active-site titration using p-nitrophenyl p'-guanidinobenzoate (Chase et al., Methods in Enzymol. (1970), XIX, 20–27). The concentration of active inhibitor is calculated assuming an equimolar interaction between inhibitor and enzyme.

To determine the specificity of hirustasin, its effect on the amidolytic activity of various serine proteinases (see Tab. 3) is determined. Therefore, proteinases are incubated with the inhibitor (1.3 mM) for 15 and for 30 min, and the residual enzyme activities are measured after addition of a suitable substrate.

Equilibrium dissociation constants ($K_i$) for the complexes of hirustasin with individual proteases are determined essentially as described by Bieth (Bull. Europ. Physopat. Resp. (1980), 16, 183–195). Briefly, increasing concentrations of the inhibitor are incubated with a constant concentration of the enzyme; the time necessary to reach equilibration of the enzyme-inhibitor complex is determined for each protease in preliminary experiments. Substrate is then added and the residual enzyme activity measured. Apparent $K_i$-values are calculated by fitting the steady state velocities to the equation for tight binding inhibitors (Morrison, Biochem. Biophys. Acta (1969), 185, 269–286) using non-linear regression analysis.

Hirustasin inhibits bovine trypsin and bovine chymotrypsin with nearly identical affinities; $K_i$ values of 7 and 6.4 nM are calculated for the complexes with trypsin and chymotrypsin, respectively (Tab. 3). In addition, hirustasin inhibits tissue kallikrein and cathepsin G with affinities in the nanomolar range ($K_i$ 13 and 2.9 nM for the complexes, respectively). Weak inhibition is observed for plasmin ($K_i$ 138 nM). In contrast, even at the highest concentration used (1.3 mM), the inhibitor has no effect on the other proteinases tested including human α-thrombin and factor Xa.

TABLE 3

| Enzyme | Species | Hirustasin $K_i$ [nM] | Antistasin $IC_{50}$ [nM] |
|---|---|---|---|
| Trypsin | Bovine | 7 | 5 |
| Chymotrypsin | Bovine | 6.4 | 0[2] |
| Cathepsin G | Human | 2.9 | d |
| Tissue kallikrein | Porcine | 13 | nd |
| Plasmin | Human | 138 | nd |
| Urokinase | Human | 0[1] | nd |
| Plasma kallikrein | Human | 0[1] | nd |
| Thrombin | Human | 0[1] | 0[2] |
| Factor Xa | Human | 0[1] | 1 |
| Pancreatic elastase | Porcine | 0[1] | 0[2] |
| Leukocyte elastase | Human | 0[1] | 0[2] |
| Subtilisin | Bact. subt. | 0[1] | nd |
| Chymase | Porcine | 0[1] | nd |

The antistasin data are from Dunwiddie et al. (J. Biol. Chem. (1989), 264, 16694–16699).
0[1]= No inhibition at 1.3 mM;
0[2]= no inhibition at 0.5 mM;
nd= not determined.

Example 4

Effect of Hirustasin on in vitro Blood Coagulation

To determine whether hirustasin inhibits the blood coagulation in vitro, its effect on the prothrombin time and the partial thromboplastin time is measured using an Amelung KC10 coagulometer (Lemgo, Germany) and the reagent sets from Behringwerke AG (Marburg, Germany) according to the guidelines of the manufacturers.

At a concentration of 1.3 mM, the inhibitor has no significant effect on these global parameters of the blood coagulation (Tab. 4). Thus, the inhibitor does not significantly inhibit factor Xa or any other proteinase involved in the blood clotting cascade.

TABLE 4

|  | Quick | Partial Thromboplastin Time |
|---|---|---|
| Buffer | 79% | 47.3 s |
| Hirustasin | 80% | 47.9 s |

Example 5

Construction of pFBY139 pFBY139 is a pUC18 derived plasmid that contains a 1048 bp BamHI fragment. This fragment contains the GAPDH promoter fused to the ATG of the α-factor leader a stuffer fragment and the α-factor terminator. The precise way the fusions were engineered enable the insertion of ORF containing fragments either at the ATG by using the EcoRI site, after the signal sequence by using a PstI site or after the α-factor leader sequence by insertion after the BglII site. The ORF to be expressed should ideally have a SalI site at their 3' end to facilitate fusion to the terminator that is preceded by a SalI site, and have no BamHI sites within their sequence, as cleavage of this plasmid at the two BamHI sites excises the whole expression cassette so that it can easily be cloned into a yeast shuttle vector.

A synthetic sequence, GATCCCCAGCTT (SEQ ID NO:2), containing a BamHI site precedes the yeast GAPDH promoter sequences from −392 to −1, where −1 is the base preceding the A of the ATG of the GAPDH ORF. This corresponds to nucleotides 287 to 653 of EMBL GENBANK accession number M13807 and nucleotides 128 to 150 of EMBL GENBANK accession number J01324, except that bases −9 to −5 are replaced by GAATT to create an EcoRI site, which is a unique site in pFBY139, just before the ATG. The ATG is provided as part of the α-1 factor pheromone signal sequence and leader, nucleotides 293 to 527 of the EMBL GENBANK accession number X01581, followed by the sequence, AGATCTTGC, which positions a BglII site, which is unique in pFBY139, just before the normal position for the LysArg KEX2 cleavage site. If fusions are required to just a signal sequence this can be achieved by using the unique PstI site which is present within the region encoding the signal sequence. The BglII site is followed by a sequence of no importance as it is always removed when the incoming ORF is cloned into the plasmid between either the EcoRI, PstI or BglII sites and the SalI site which marks the end of the stuffer fragment and the beginning of the α-1 factor pheromone terminator sequences, nucleotides 825 to 1100 of EMBL GENBANK accession number X01581. This is followed immediately by the sequence AATTCGGATCC (SEQ. ID. NO:20) which encodes the BamHI site that bounds this end of the expression cassette.

This plasmid can be constructed using polymerase chain reaction (PCR) fragments from yeast genomic DNA.

All oligonucleotides used in the PCR reaction are synthesized using an automatic DNA synthesizer. The PCR reactions are carried out in a PCR unit from Perkin Elmer under the following conditions:

20 mM of the oligonucleotides in question are incubated in 0.1 ml buffer (10 mM Tris-HCl, pH 8.3, 50 mM KCl, 1.5 mM MgCl$_2$) with 2.5 units of Taq DNA-polymerase and 0.2 mM of dATP, dCTP, dTTP and dGTP. The reactions are incubated for 30 cycles: 30 sec at 92° C., for 1 min at 42° C. and at 72° C. for 1 min.

The fragment comprising the GAPDH promoter is generated from genomic yeast DNA using the PCR fragments SEQ ID NO:4 and SEQ ID NO:5

SEQ ID NO:4 5' GCATGGATCCCAGCTTAGTTCATAGGTCCATTCTCTTAGCGC 3'

SEQ ID NO:5 5' CTCGGAATTCTTATGTGTGTTTATTCGAAACTAAGTTC 3' and subsequent cleavage with BamHI and EcoRI.

The fragment comprising most of the α-factor signal and leader sequences is generated from genomic yeast DNA using the PCR fragments SEQ ID NO:6 and SEQ ID NO:7

SEQ ID NO:6 5' GTGCGAATTCAAAATGAGATTTCCTTCAATTTTTACTGCAG 3'

SEQ ID NO:7 5' CAAAGTCGACTTTATCCAGCAAGATCTCTTCTTCTTTAGCAGCAATGC 3'

The fragment comprising the α-factor terminator is generated from genomic yeast DNA using the PCR fragments SEQ ID NO:8 and SEQ ID NO:9

SEQ ID NO:8 5' GAAGAGATCTTGCTGGATAAAGTCGACTTTGTTCCCACTGTACTTTTAGC 3'

SEQ ID NO:9 5' CCGGGGATCCGAATTAATTCTCTTAGGATTCG 3'

The fragment comprising most of the α-factor signal and leader sequences and the fragment comprising the α-factor terminator are mixed and reamplified in a PCR reaction with SEQ ID NO:6 and SEQ ID NO:8 and cut with EcoRI and BamHI. The later amplified fragment and the fragment comprising the GAPDH promoter are cloned into pTZ18R cut with BamHI and treated with bacterial alkaline phosphatase to create pFBY139.

Example 6

Construction of pFBY166 pFBY166 is a pUC18 derived plasmid that contains a 1085 bp BamHI fragment. This fragment contains the CUP1 promoter fused to the ATG of the α-factor leader a stuffer fragment and the α-factor terminator. The precise way the fusions were engineered enable the insertion of ORF containing fragments either at the ATG by using the EcoRI site, after the signal sequence by using a PstI site or after the α-factor leader sequence by insertion after the BglII site. The ORF to be expressed should ideally have a SalI site at their 3' end to facilitate fusion to the terminator that is preceded by a SalI site, and have no BamHI sites within their sequence, as cleavage of this plasmid at the two BamHI sites excises the whole expression cassette so that it can easily be cloned into a yeast shuttle vector.

The plasmid is identical to pFBY139 except that the BamHI to EcoRI fragment containing the GAPDH promoter is replaced by a fragment, corresponding to nucleotides 1080 to 1505 of EMBL GENBANK accession number K02204, which contains the CUP1 promoter which allows expression in a copper regulated manner.

The fragment comprising the CUP1 promoter is generated from genomic yeast DNA using the PCR fragments SEQ ID NO:10 and SEQ ID NO:11

SEQ ID NO:10 5' TAGAGGATCCCCATTACCGACATTTGGGCGCTATACGTGC 3'

SEQ ID NO:12 5' CGACGAATTCACAGTTTGTTTTTCTTAATATCTATTTCG 3' and subsequent cleavage with BamHI and EcoRI.

The fragments comprising most of the α-factor signal and leader sequences and the fragment comprising the α-factor terminator are generated, amplified and cut as described in example 5 and subsequently cloned together with the fragment comprising the CUP1 promoter into pTZ18R cut with BamHI and treated with bacterial alkaline phosphatase to create pFBY166.

Example 7

Construction of pHE 168: Expression of Hirustasin Under Control of the Regulated CUP1 Promoter A synthetic gene encoding hirustasin in preferred yeast codon usage is assembled from 3 synthetic oligonucleotides in a PCR reaction. In addition, the gene is extended at its 5' end to provide for convenient in-frame fusion to the α-factor leader in plasmid pFBY 166.

The following 3 oligonucleotides are synthesized using an automatic DNA synthesizer:

5'-AAAGATCTTG CTGGATAAAA GAACCCAAGG TAACACCTGT GGTGGTGAAA
CCTGTTCTGC CGCCCAAGTT TGTTTGAAGG GTAAGTGTGT -3'
(SEQ ID NO:12)

5'-GTATTCACAA CCGTTTTCGT CCTTCTTCAA ACCGTACTTA CAACGAATAC
GACAGTGAAC TTCGTTACAA ACACACTTAC CCTTCAAACA -3'
(SEQ ID NO:13)

5'-TTGTCGACTC ATTGAGAGGC CTTGGCACAA GAACATGGGT ATTCACAACC
GTTTTCGT -3'
(SEQ ID NO:14)

Of these 3 oligonucleotides a 198 bp fragment is assembled in the following polymerase chain reaction (PCR) using the PCR unit from Perkin Elmer and the following conditions:

20 mM of oligonucleotides 1 and 3 and 20 nM of oligonucleotide 2 are incubated in 0.1 ml buffer (10 mM Tris-HCl, pH 8.3, 50 mM KCl, 1.5 mM MgCl$_2$) with 2.5 units of Taq DNA-polymerase and 0.2 mM of dATP, dCTP, dTTP and dGTP. The reaction is incubated for 30 cycles: 30 sec at 92° C., for 1 min at 42° C. and at 72° C. for 1 min.

The 198 bp PCR fragment is isolated over a 2% agarose gel, restricted with BglII and SalI and ligated into BglII and SalI cut pFBY 166 (supra). E. coli HB101 is transformed with the resulting plasmid pHE168. The transformed E. coli strain is designated E. coli/pHE168.

Correct fusion of the PCR fragment to the α-factor leader and correct sequence of the hirustasin ORF is confirmed by sequencing. The complete expression cassette containing the yeast ORF and the α-factor terminator is shown in SEQ ID NO:3.

Example 8

Construction of pHE 170 and 170R 2 Micron Vectors with the Hirustasin Expression Cassette For the expression in yeast pDP34 is used as vector. pDP34 (EP-A-340 170, FIG. 3 therein) is a yeast-E. coli shuttle vector with the ampicillin resistance marker for E. coli and the URA3 and dLEU2 yeast selective markers. It contains the complete 2 micron sequences in the A form and is REP1, REP2 and FLP proficient.

Plasmid pDP34 is digested with BamHI and the sticky ends are dephosphorylated by alkaline phosphatase treatment. pHE168 is digested with BamHI and the 1146 bp fragment containing the complete hirustasin expression cassette ligated into BamHI-cut pDP 34. *E. coli* HB 101 is transformed with the resulting plasmids pHE 170 and 170R. Orientation of the insert is tested by digestion with SalI. pHE 170 contains the hirustasin expression cassette in a clockwise orientation with respect to dLEU2, pHE 170R in anticlockwise orientation with respect to the dLEU2 marker.

Example 9

Construction of pHE 169 Expression of Hirustasin Under Control of the Constitutive GAPDH Promoter The 198 bp PCR fragment encoding hirustasin (supra) is digested with BglII and SalI and ligated into BglII and SalI cut vector pFBY 139. *E. coli* HB 101 is transformed with the resulting plasmid pHE169. The transformed *E. coli* strain is designated *E. coli*/pHE169. Correct fusion of the PCR fragment to the α-factor leader and correct sequence of the hirustasin ORF is confirmed by sequencing. The expression cassette is identical to the one shown in SEQ ID NO:3 except for the GAPDH 400 bp promoter fragment instead of the CUPI promoter (SEQ ID NO:2).

Example 10

Construction of pHE 171 and pHE 171R 2 Micron Vectors with the Hirustasin Expression Cassette In analogy to example 9 (supra) the 1109 bp BamHI fragment containing the hirustasin expression cassette is excised from pHE 169 by BamHI digestion and inserted into BamHI cut pDP 34. *E. coli* HB 101 is transformed with the resulting plasmids pHE 171 and pHE171R. Orientation of the insert is tested by digestion with SalI. pHE 171 contains the hirustasin expression cassette in a clockwise orientation with respect to dLEU2, pHE 171R in an anticlockwise orientation.

Example 11

Construction of pHE 172 The Hirustasin ORF Fused to the Invertase Signal Sequence (SUC2)

To provide for an alternative secretion system, the hirustasin ORF is fused to the signal sequence of the yeast invertase gene SUC2.

The 2 following oligonucleotides are made:

5'-AAGAATTCAT GCTTTTGCAA GCTTTCCTTT TCCTTTTGGC TGGTTTTGCA
GCCAAAATAT CTGCAACCCA AGGTAACACC TGTG -3'
(SEQ ID NO:15)

5'-TTGTCGACTC ATTGAGAGGC-3'
(SEQ ID NO:16)

pHE 168 is used as template DNA for a polymerase chain reaction as described in example 7. 20 ng of template pHE 168 is incubated with 20 mM of the oligonucleotide primers under the experimental conditions as in example 7.

The 237 bp amplified PCR fragment is isolated over a 2% agarose gel, restricted with EcoRI and SalI and ligated into EcoRI and SalI cut vector pFBY 166.

*E. coli* HB 101 is transformed with the resulting plasmid pHE 172. Correct sequence of the SUC2 signal sequence-hirustasin fusion is confirmed by sequencing.

Example 12

Construction of pHE 173 and pHE 173R 2 Micron Vectors with the Hirustasin Expression Cassette with the SUC2 Signal Sequence In analogy to example 8, the 945 bp BamHI fragment containing the hirustasin expression cassette is excised from pHE 172 by BamHI digestion and inserted into BamHI cut pDP 34. *E. coli* HB 101 is transformed with the resulting plasmids pHE 173 and pHE 173R. Orientation of the insert is tested by digestion with SalI. pHE 173 contains the hirustasin expression cassette in a clockwise orientation with respect to dLEU2, pHE 173R in an anticlockwise orientation.

Example 13

Construction of *Saccharomyces cerevisiae* Strain TR 1456

*Saccharomyces cerevisiae* strain TR1456 is constructed as disclosed in EP-A-341 215. Starting with *Saccharomyces cerevisiae* strain H449, in two subsequent series of experiments the two carboxypeptidases yscα and yscY are removed from strain H449 by disruption of their encoding genes KEX1 and PRC1, respectively. First, the gene encoding yscα, KEX1, is disrupted.

For this purpose, strain H449 is transformed with a DNA fragment encoding the KEX1 gene, with the full URA3 gene inserted in the middle of the KEX1 coding region. Uracil prototrophic transformants are selected and tested for the absence of yscα activity. Next, the URA3 gene inserted at the KEX1 locus is disrupted by transformation with a plasmid containing a disrupted version of the gene, URA3D5 (see EP-A-341 215). Transformants which are uracil auxotrophic are selected and in the following step disrupted in their endogenous PRC1 gene coding for the carboxypeptidase yscY. The experiment is carried out in a totally analogous manner as described for the disruption of KEX1. The finally resulting isogenic derivative of strain H449 is called TR1456 and has the following genotype:
TR1456=MATa, leu2-3, 112, ura3, prb1, kex1::ura3, prc1::ura3, [cir°]

Example 14

Transformation of Strain TR 1456 with Plasmids pHE 170, 170R, 171, 171R, 173, 173R The plasmids pHE 170, 170R, 171, 171R, 173, 173R are introduced into the host strain TR1456 using the transformation protocol described by Hinnen et al. (Proc. Natl. Acad. Sci. USA (1978), 75, 1929). Further details of the procedure are as described in EP-A-341 215. Transformed yeast cells are selected on yeast minimal medium, supplemented with leucine and lacking uracil. Single transformed yeast clones are isolated and referred to as:

*Saccharomyces cerevisiae* TR 1456/pHE 170
*Saccharomyces cerevisiae* TR 1456/pHE 170R
*Saccharomyces cerevisiae* TR 1456/pHE 171
*Saccharomyces cerevisiae* TR 1456/pHE 171R
*Saccharomyces cerevisiae* TR 1456/pHE 173
*Saccharomyces cerevisiae* TR 1456/pHE 173R Example 15

Hirustasin Secretion by TR 1456 Transformed with Plasmids pHE 170, 171, 173

Cells of *Saccharomyces cerevisiae* TR 1456/pHE 170, 170R, 171, 171R, 173, 173R are each grown in two subsequent precultures in 20 ml synthetic medium composed of:

| | |
|---|---|
| 6.7 g/l | Difco Yeast Nitrogen Base (without amino acids) |
| 10 g/l | L-asparagine |
| 1 g/l | L-histidine |
| 20 g/l | glucose |
| 0.02 g/l | L-leucine |

The pH of the medium is adjusted to 5.8. The first preculture is grown for 60 h at 28° C. and 180 r.p.m. The second preculture is inoculated with 2% (volume per volume) of the first preculture and incubated for 24 h at 28° C. and 180 r.p.m.

The medium of the main culture is composed of:

| | |
|---|---|
| 5 g/l | peptone |
| 10 g/l | yeast extract |
| 20 g/l | glucose |
| 40 g/l | sucrose |
| 3 g/l | ammonium sulfate |
| 2 g/l | potassium dihydrogenphosphate |
| 0.5 g/l | magnesium sulfate heptahydrate |
| 0.1 g/l | sodium chloride |
| 0.1 g/l | calcium chloride |
| $10^{-5}$ g/l | biotin |

The main culture (100 ml medium) is inoculated with about $10^6$ cells/ml and incubated for 72 h at 28° C. and 180 r.p.m.

Immediately following the inoculation, sterile copper sulfate is added at a concentration of 1 mM to *Saccharomyces cerevisiae* cultures TR 1456/pHE 170, 170R and TR 1456/pHE 173, 173R. TR 1456/pHE 171, 171R are grown without copper.

At the end of the fermentation, aliquots of the cultures are taken, the cells are removed by centrifugation and the culture supernatant is analyzed for hirustasin activity in an enzymatic assay as described in example 3.

We claim:

1. A substantially purified polypeptide comprising the amino acid sequence as given in SEQ ID NO:1.

2. A polypeptide comprising a fragment of the polypeptide according to claim 1, wherein said fragment consists of residues 1–54 of SEQ ID NO:1.

3. A polypeptide according to claim 1 further comprising a detectable marker selected from the group consisting of a fluorescent marker, chemiluminescent marker, radioactive marker, avidin and biotin.

4. A pharmaceutical composition comprising a polypeptide according to claim 1 and auxiliaries, carriers, or diluents.

5. A method of therapeutic treatment of a disease or clinical syndrome of the human or animal body related to the action of serine proteases, said method comprising treating with a therapeutically effective amount of a pharmaceutical composition comprising the polypeptide of claim 1 or a pharmacologically acceptable salt thereof.

6. A method of therapy according to claim 5, wherein said disease or clinical syndrome is selected from the group consisting of thromboses, embolism, hypertension, cancer, blood coagulation, thromboembolisms, post-operative thromboses, acute shock, consumptive coagulopathies or coagulation associated with hemodialysis, hemoseparations, and extracorporeal blood circulation.

7. A method for inhibiting blood coagulation, said method comprising treating with a therapeutically effective amount of the polypeptide of claim 1.

8. A method for managing hypertension comprising administering a therapeutically effective amount of the polypeptide of claim 1.

9. A substantially purified polypeptide comprising the amino acid sequence as given in SEQ ID NO:1 or a functional fragment thereof, wherein said functional fragment thereof inhibits serine proteinases and neither affects the catalytic activity of isolated factor Xa nor the blood coagulation cascade in vitro.

10. A polypeptide according to claim 9 further comprising a detectable marker selected from the group consisting of a fluorescent marker, chemiluminescent marker, radioactive marker, avidin and biotin.

11. A pharmaceutical composition comprising a polypeptide according to claim 9 and auxiliaries, carriers, or diluents.

12. A method of therapeutic treatment of a disease or clinical syndrome of the human or animal body related to the action of serine proteases, said method comprising treating with a therapeutically effective amount of a pharmaceutical composition comprising the polypeptide of claim 9 or a pharmacologically acceptable salt thereof.

13. A method of therapy according to claim 12, wherein said disease or clinical syndrome is selected from the group consisting of thromboses, embolism, hypertension, cancer, blood coagulation, thromboembolisms, post-operative thromboses, acute shock, consumptive coagulopathies, or coagulation associated with hemodialysis, hemoseparations, and extracorporeal blood circulation.

14. A method for inhibiting blood coagulation, said method comprising treating with a therapeutically effective amount of the polypeptide of claim 9.

15. A method for managing hypertension comprising administering a therapeutically effective amount of the polypeptide of claim 9.

* * * * *